United States Patent
Li et al.

(10) Patent No.: US 12,315,633 B2
(45) Date of Patent: May 27, 2025

(54) MEDICAL IMAGE PROCESSING APPARATUS AND MEDICAL IMAGE PROCESSING METHOD

(71) Applicant: Hitachi, Ltd., Tokyo (JP)

(72) Inventors: Yun Li, Tokyo (JP); Hanae Yoshida, Tokyo (JP); Mayumi Suzuki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 527 days.

(21) Appl. No.: 17/714,331

(22) Filed: Apr. 6, 2022

(65) Prior Publication Data

US 2022/0344047 A1 Oct. 27, 2022

(30) Foreign Application Priority Data

Apr. 27, 2021 (JP) .................................. 2021-074718

(51) Int. Cl.
*G06T 7/00* (2017.01)
*G16H 50/20* (2018.01)

(52) U.S. Cl.
CPC ........... *G16H 50/20* (2018.01); *G06T 7/0012* (2013.01); *G06T 2207/30096* (2013.01)

(58) Field of Classification Search
CPC ........ G16H 50/20; G16H 30/40; G16H 50/70; G06T 7/0012; G06T 2207/30096; G06T 2207/10081; G06T 2207/20084; G06T 2207/30048; G06N 3/0464; G06N 3/09
See application file for complete search history.

(56) References Cited

U.S. PATENT DOCUMENTS

| | | | |
|---|---|---|---|
| 10,980,493 B2 * | 4/2021 | Osawa | G06T 15/08 |
| 2018/0293729 A1 | 10/2018 | Hashimoto | |
| 2021/0166382 A1 * | 6/2021 | Kanada | A61B 6/03 |
| 2022/0392619 A1 * | 12/2022 | Ichinose | G06T 1/00 |
| 2023/0197253 A1 * | 6/2023 | Nakamura | A61B 6/00 382/128 |
| 2023/0386033 A1 * | 11/2023 | Yoshida | G06T 7/13 |

FOREIGN PATENT DOCUMENTS

JP 2018-175217 A 11/2018

* cited by examiner

*Primary Examiner* — Sean M Conner
*Assistant Examiner* — Renae A Bitor
(74) *Attorney, Agent, or Firm* — MATTINGLY & MALUR, PC (57) ABSTRACT

A medical image processing apparatus and a medical image processing method that can improve extraction accuracy of a tumor region included in a diagnosis target image are provided. The medical image processing apparatus configured to extract a predetermined region from a diagnosis target image includes: an organ extraction unit configured to extract an organ region from the diagnosis target image; and a tumor extraction unit generated by executing machine learning using a known tumor region included in each medical image group as teacher data and using an organ region extracted from the medical image group and the medical image group as input data. The tumor extraction unit is configured to extract a tumor region from the diagnosis target image using the organ region extracted from the diagnosis target image by the organ extraction unit.

5 Claims, 11 Drawing Sheets

TOMOGRAPHIC IMAGE

FIG. 5C

EXTRACTION OF ORGAN REGION

FIG. 5D

EXTRACTION OF TUMOR REGION

FIG. 5E

FUSION OF REGIONS

MEDICAL IMAGE PROCESSING APPARATUS AND MEDICAL IMAGE PROCESSING METHOD

CLAIM OF PRIORITY

The present application claims priority from Japanese Patent Application JP 2021-074718 filed on Apr. 27, 2021, the content of which is hereby incorporated by reference into this application.

BACKGROUND OF THE INVENTION

1. Field of the Invention

The present invention relates to a medical image processing apparatus and a medical image processing method for extracting a tumor included in a medical image.

2. Description of the Related Art

A medical image capturing device that is typified by an X-ray computed tomography (CT) device or the like is a device that captures an image of a morphology of a lesion or the like, and the obtained medical image is used for image diagnosis or treatment planning. In order to execute appropriate image diagnosis or treatment planning, it is important to classify tissues and lesions with high accuracy.

JP-A-2018-175217 describes an image processing apparatus capable of classifying regions of tissues and lesions included in a medical image with high accuracy. Specifically, the image processing apparatus identifies, using a determiner that executes machine learning using a tomographic image as teacher data, a type of a tissue or a lesion to which pixels of tomographic images in different cross-sectional directions belong, and re-identifies the type of a lesion or the like by evaluating a pixel common to a plurality of tomographic images. In the tomographic image, the type of a tissue or a lesion is known.

However, in JP-A-2018-175217, only a determiner that individually executes machine learning on the type of a tissue or a lesion, and it is insufficient to extract a lesion such as a tumor with higher accuracy.

SUMMARY OF THE INVENTION

An object of the invention is to provide a medical image processing apparatus and a medical image processing method that can improve extraction accuracy of a tumor region included in a diagnosis target image.

In order to achieve the above object, the invention provides a medical image processing apparatus configured to extract a predetermined region from a diagnosis target image. The medical image processing apparatus includes: an organ extraction unit configured to extract an organ region from the diagnosis target image; and a tumor extraction unit generated by executing machine learning using a known tumor region included in each medical image group as teacher data and using an organ region extracted from the medical image group and the medical image group as input data. The tumor extraction unit is configured to extract a tumor region from the diagnosis target image using the organ region extracted from the diagnosis target image by the organ extraction unit.

The invention provides a medical image processing method for extracting a predetermined region from a diagnosis target image. The medical image processing method includes: an organ extraction step of extracting an organ region from the diagnosis target image; and a tumor extraction step of extracting a tumor region from the diagnosis target image using the organ region extracted from the diagnosis target image in the organ extraction step.

According to the invention, a medical image processing apparatus and a medical image processing method that can improve extraction accuracy of a tumor region included in a diagnosis target image can be provided.

DESCRIPTION OF THE PREFERRED EMBODIMENTS

Hereinafter, embodiments of a medical image processing apparatus and a medical image processing method according to the invention will be described with reference to accompanying drawings. In the following description and the accompanying drawings, components having the same function and structure are denoted by the same reference numerals, and repeated description thereof will be omitted.

First Embodiment

Figure 1:
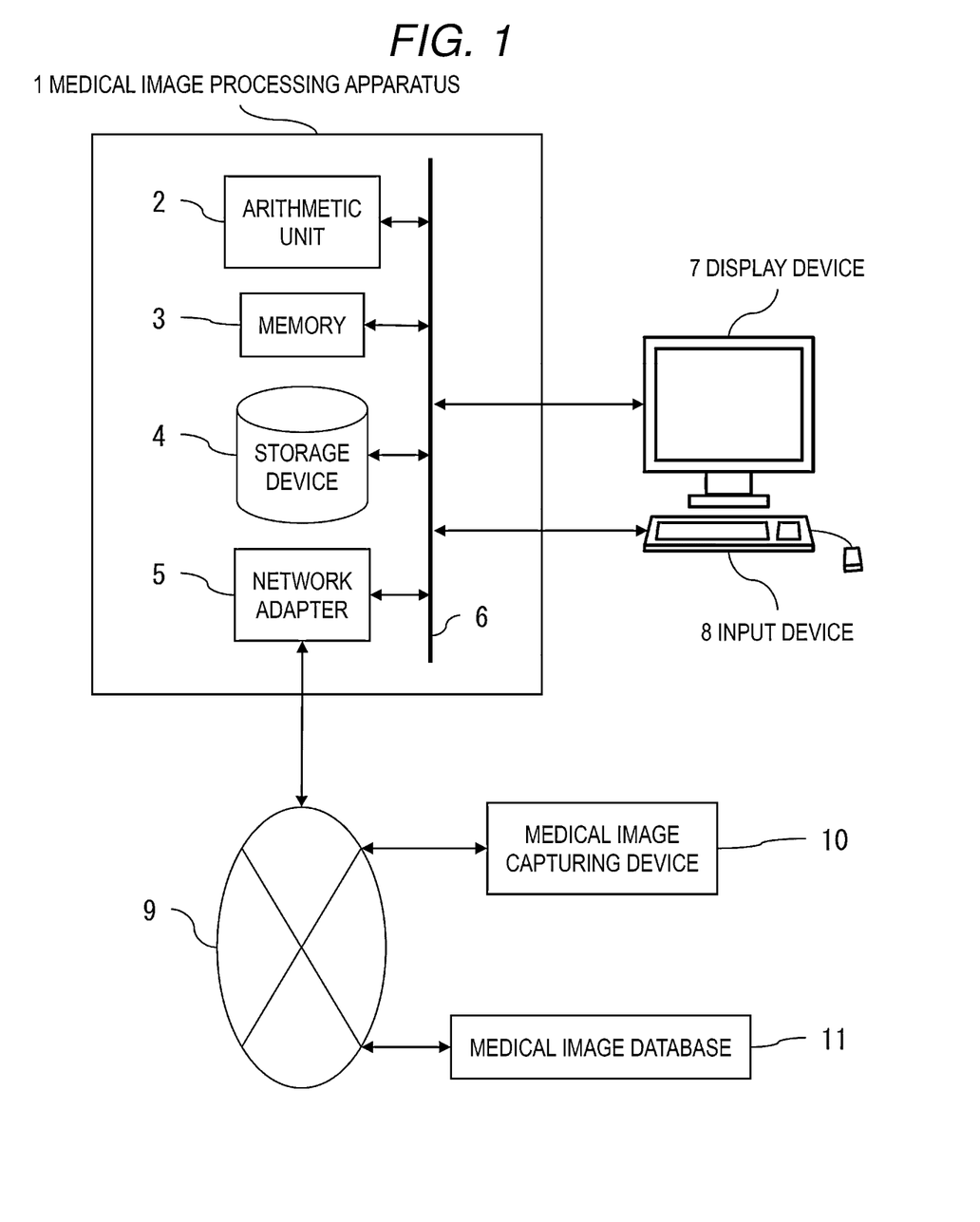
FIG. 1 is an overall configuration diagram of a medical image processing apparatus.

FIG. 1 is a diagram showing a hardware configuration of a medical image processing apparatus 1. The medical image processing apparatus 1 includes an arithmetic unit 2, a memory 3, a storage device 4, and a network adapter 5, which are connected via a system bus 6 so as to transmit and receive a signal. The medical image processing apparatus 1 is connected to a medical image capturing device 10 and a medical image database 11 via a network 9 so as to transmit and receive a signal. Further, a display device 7 and an input device 8 are connected to the medical image processing apparatus 1. Here, "so as to transmit and receive a signal" indicates a state of being able to transmit and receive a signal to and from each other or from one to the other regardless of whether the connection is electrically or optically wired or wireless.

The arithmetic unit 2 is a device that controls operations of components, and is specifically a central processing unit (CPU), a micro processor unit (MPU), or the like. The arithmetic unit 2 loads a program stored in the storage device 4 and data necessary for executing the program into the memory 3 and executes the program, and executes various types of image processing on the medical image. The memory 3 stores the program to be executed by the arithmetic unit 2 and a progress of arithmetic processing. The storage device 4 is a device that stores the program to be executed by the arithmetic unit 2 and the data necessary for executing the program, and is specifically a hard disk drive (HHD), a solid state drive (SSD), or the like. The network adapter 5 is used for connecting the medical image processing apparatus 1 to the network 9 such as a local area network (LAN), a telephone line, or the Internet. Various data to be processed by the arithmetic unit 2 may be transmitted to and received from the outside of the medical image processing apparatus 1 via the network 9 such as the LAN.

The display device 7 is a device that displays a processing result or the like of the medical image processing apparatus 1, and is specifically a liquid crystal display, a touch panel, or the like. The input device 8 is an operation device for an operator to give an operation instruction to the medical image processing apparatus 1, and is specifically a keyboard, a mouse, a touch panel, or the like. The mouse may be another pointing device such as a trackpad or a trackball.

The medical image capturing device 10 is a device that captures a tomographic image or the like of the subject, and for example, is an X-ray CT device, a magnetic resonance imaging (MRI) device, and a positron emission tomography (PET) device. The medical image database 11 is a database system that stores the medical images such as the tomographic image captured by the medical image capturing device 10 and a corrected image obtained by executing image processing on the tomographic image.

Figure 2:
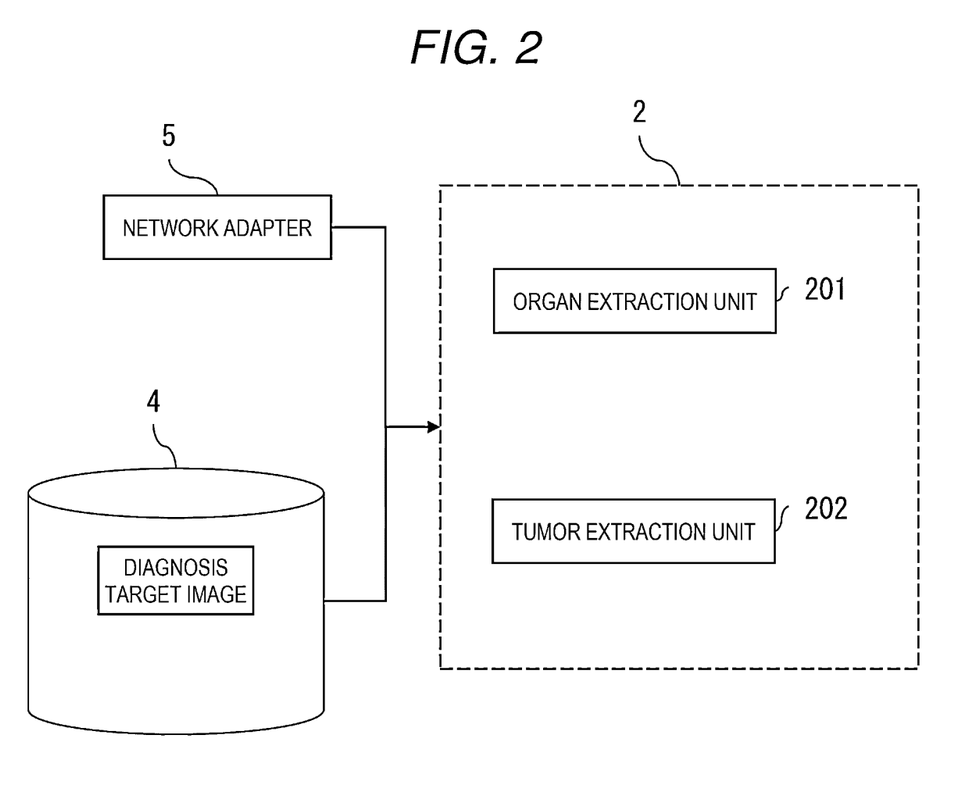
FIG. 2 is a diagram showing a functional block according to a first embodiment.

A functional block diagram according to a first embodiment will be described with reference to FIG. 2. Each function shown in FIG. 2 may be implemented by dedicated hardware using an application specific integrated circuit (ASIC), a field-programmable gate array (FPGA), or the like, or may be implemented by software operating on the arithmetic unit 2. In the following description, a case will be described in which each function according to the first embodiment is implemented by the software.

In the first embodiment, an organ extraction unit 201 and a tumor extraction unit 202 are provided. The storage device 4 stores a diagnosis target image or the like. The diagnosis target image is a medical image captured by the medical image capturing device 10 and is a diagnosis target. The diagnosis target image may be a tomographic image or a volume image. Hereinafter, each component will be described.

The organ extraction unit 201 extracts an organ region from the diagnosis target image based on a pixel value of a pixel included in the diagnosis target image. The extracted organ region is classified into, for example, a heart, a lung, a body surface, or the like. The organ extraction unit 201 may include, for example, a convolutional neural network (CNN) generated by executing machine learning using a large number of medical images including a known organ region as input data and the known organ region as teacher data.

The tumor extraction unit 202 is generated by executing machine learning using a known tumor region included in the large number of medical images as teacher data to extract a tumor region from the diagnosis target image, and includes, for example, the CNN.

Figure 3:
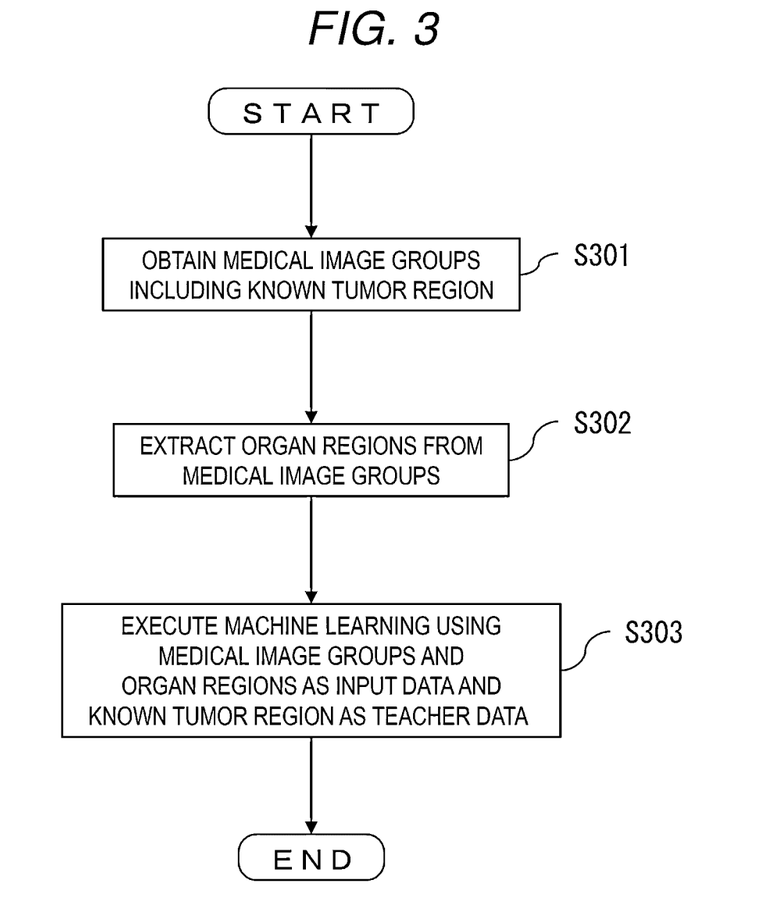
FIG. 3 is a diagram showing an example of a processing flow for generating a tumor extraction unit.

An example of a processing flow for generating the tumor extraction unit 202 will be described for each step with reference to FIG. 3.

S301

Medical image groups including the known tumor region are obtained. That is, each pixel included in the medical images is assigned an identifier indicating whether the pixel is a tumor region.

S302

An organ region is extracted from each medical image group obtained in S301. That is, each pixel included in the medical images is assigned an identifier indicating whether the pixel is an organ region, and an identifier indicating which organ the pixel is further assigned to the pixel which is the organ region.

In the extraction of the organ region from the medical images, the organ extraction unit 201 may be used. When the known organ region is included in the medical images, an identifier of each pixel is used.

S303

The tumor extraction unit 202 is generated by executing machine learning using the medical image groups obtained in S301 and the organ region extracted in S302 as input data and the known tumor region included in the medical images as teacher data. Specifically, a weight value of each path of an intermediate layer connecting an input layer and an output layer is adjusted such that output data output from the output layer matches the teacher data when the input data is input to the input layer.

As described above, the tumor extraction unit 202 is generated by the described processing flow. Since the generated tumor extraction unit 202 executes machine learning using not only the medical image groups including the known tumor region but also the organ region extracted from each medical image group as input data, the tumor extraction unit 202 includes, as knowledge, relation between the tumor region and the organ region, for example, relative positional relation between the tumor region and the organ region.

Figure 4:
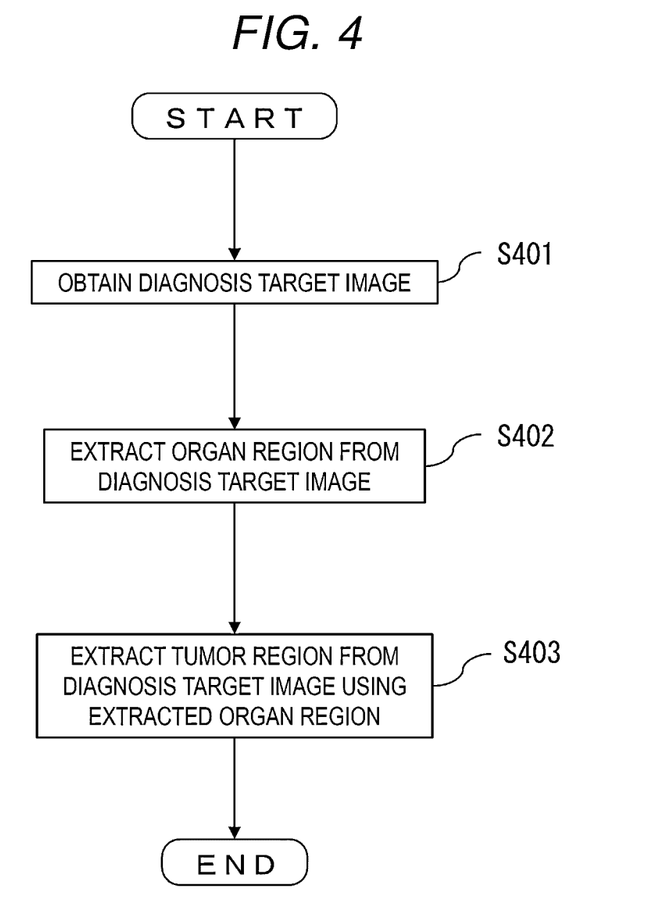
FIG. 4 is a diagram showing an example of a processing flow according to the first embodiment.

An example of a processing flow for extracting the tumor region from the diagnosis target image according to the first embodiment will be described for each step with reference to FIG. 4.

S401

Figure 5A:
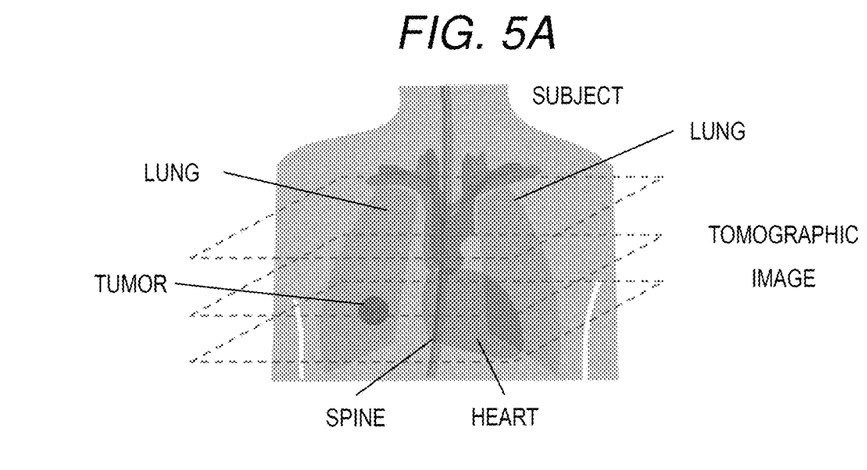
FIG. 5A is a diagram showing image capturing of a chest of a subject.
Figure 5B:
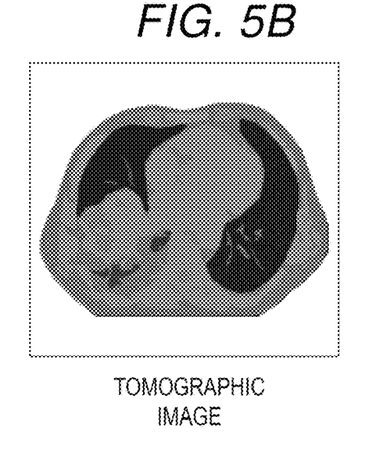
FIG. 5B is a diagram showing an example of a tomographic image.

The diagnosis target image that is a medical image of a diagnosis target is obtained. The diagnosis target image is, for example, a tomographic image obtained by capturing an image of the chest of the subject shown in FIG. 5A by the medical image capturing device 10, and is transmitted via the network adapter or read from the storage device 4. FIG. 5B shows the tomographic image of the chest. The obtained diagnosis target image is not limited to one tomographic image, and may be a plurality of tomographic images, or a volume image.

S402

Figure 5C:
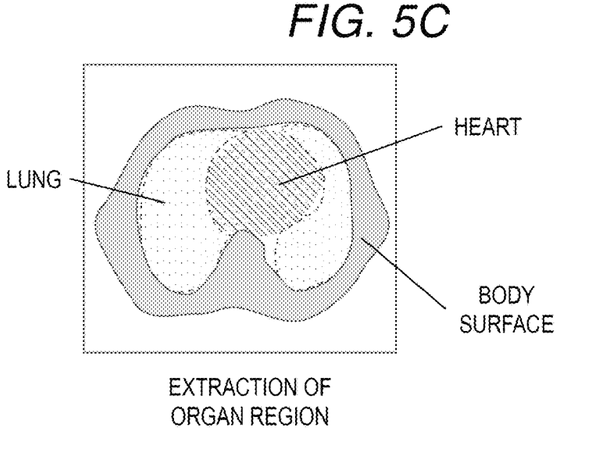
FIG. 5C is a diagram showing an example of an extracted organ region.

The organ extraction unit 201 extracts an organ region from the diagnosis target image obtained in S401. The extracted organ region is classified into a heart, a lung, a body surface, and the like as shown in FIG. 5C.

S403

Figure 5D:
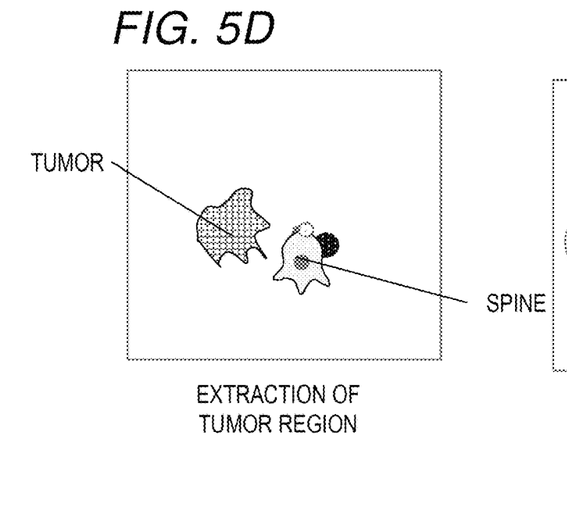
FIG. 5D is a diagram showing an example of an extracted tumor region.
Figure 5E:
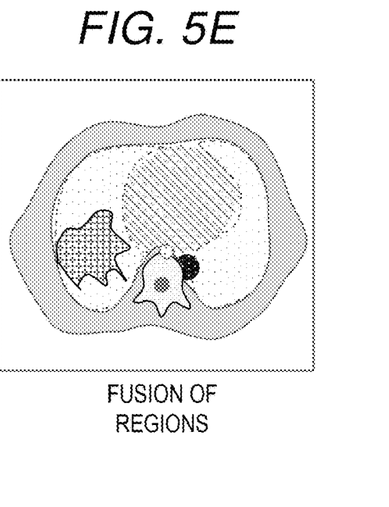
FIG. 5E is a diagram showing an example of an image obtained by fusing the organ region and the tumor region.

The tumor extraction unit 202 extracts a tumor region from the diagnosis target image using the organ region extracted in S402. FIG. 5D shows the tumor region extracted from the tomographic image of the chest. Along with the extraction of the tumor region, the organ region extracted in S402 may be subdivided, and for example, a spine may be extracted. As shown in FIG. 5E, the extracted tumor region and the organ region may be fused.

As described above, according to the described processing flow, the tumor region can be extracted from the diagnosis target image. In particular, since the tumor extraction unit 202 includes relation between the tumor region and the organ region as knowledge, the tumor extraction unit 202 can extract the tumor region with high accuracy as compared with a determiner that only executes machine learning using a known tumor region as teacher data.

Figure 6:
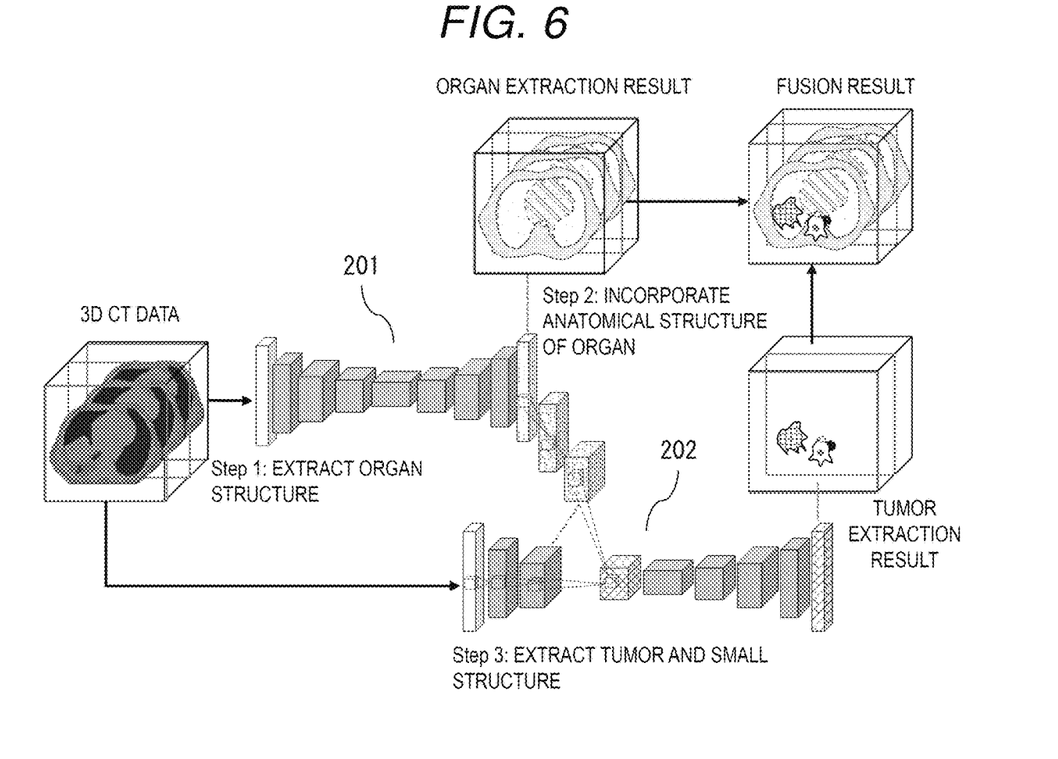
FIG. 6 is a diagram showing an example of model configurations of an organ extraction unit and the tumor extraction unit.

An example of model configurations of the organ extraction unit 201 and the tumor extraction unit 202 will be described with reference to FIG. 6. The organ extraction unit 201 and the tumor extraction unit 202 that are generated by executing machine learning are configured based on the CNN. When three-dimensional CT data, which is the diagnosis target image, is input to the input layer of the organ extraction unit 201, an organ region is extracted. The extracted organ region is incorporated into the tumor extraction unit 202, and is used when the tumor extraction unit 202 extracts a tumor region from the diagnosis target image. The extracted organ region may be incorporated into the intermediate layer of the tumor extraction unit 202, or may be input to the input layer. Finally, the organ region extracted by the organ extraction unit 201 and the tumor region extracted by the tumor extraction unit 202 are fused.

Figure 7:
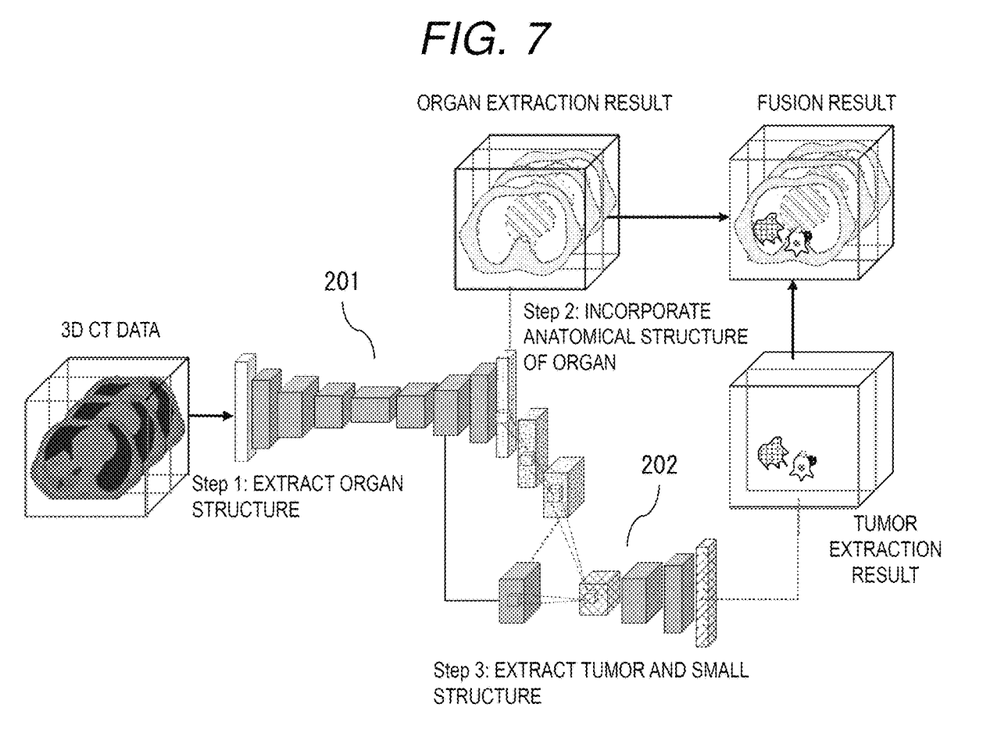
FIG. 7 is a diagram showing another example of the model configurations of the organ extraction unit and the tumor extraction unit.

Another example of the model configurations of the organ extraction unit 201 and the tumor extraction unit 202 will be described with reference to FIG. 7. In the example in FIG. 6, a model of the organ extraction unit 201 and a model of the tumor extraction unit 202 are divided, whereas in the example in FIG. 7, the organ extraction unit 201 and the tumor extraction unit 202 are configured by one model, and an extraction result of the organ region is incorporated via a layer inside a network and used for the extraction of the tumor region. Since the size of the models can be reduced according to the configuration shown in FIG. 7, it is easy to implement the medical image processing apparatus 1.

Second Embodiment

In the first embodiment, the tumor region is extracted from the diagnosis target image by the tumor extraction unit 202 that is generated by executing machine learning using not only the medical image groups including the known tumor region but also the organ region extracted from each medical image group as input data. In a second embodiment, calculation of a feature amount related to the extracted tumor region will be described. The feature amount related to the tumor region can be used to support the image diagnosis and the treatment planning. Since the hardware configuration of the medical image processing apparatus 1 according to the second embodiment is the same as that according to the first embodiment, the description thereof will be omitted.

Figure 8:
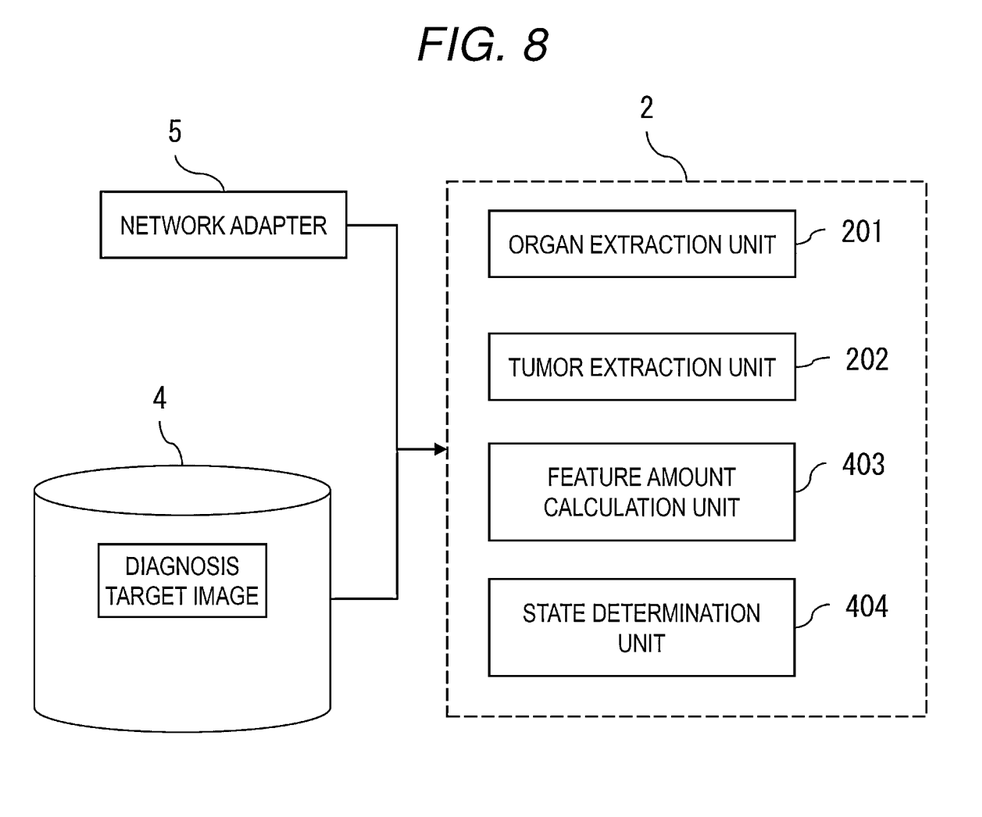
FIG. 8 is a diagram showing a functional block according to a second embodiment.

A functional block diagram according to the second embodiment will be described with reference to FIG. 8. Similar to the first embodiment, each function shown in FIG. 8 may be implemented by dedicated hardware using an ASIC, an FPGA, or the like, or may be implemented by software operating on the arithmetic unit 2. In the following description, a case will be described in which each function according to the second embodiment is implemented by the software.

In the second embodiment, similar to the first embodiment, the organ extraction unit 201 and the tumor extraction unit 202 are provided, and a feature amount calculation unit 403 and a state determination unit 404 are further provided. Hereinafter, the feature amount calculation unit 403 and the state determination unit 404 that are added to the configuration according to the first embodiment will be described.

The feature amount calculation unit 403 calculates a feature amount related to the tumor region extracted from the diagnosis target image. The feature amount related to the tumor region includes a tumor property feature amount that is a feature amount related to the tumor region itself, a tumor-organ feature amount that is a feature amount representing the relation between the tumor region and the organ region, and an intermediate layer feature amount that is a feature amount used in an intermediate layer of the tumor extraction unit 202.

The state determination unit 404 determines a state of the tumor region based on the feature amount calculated by the feature amount calculation unit 403. The state of the tumor region includes a size, an infiltration stage, classification, a development stage, and the like of the tumor.

An example of a processing flow for extracting a tumor region from a diagnosis target image and calculating the feature amount related to the tumor region according to the second embodiment will be described for each step with reference to FIG. 9. S301 to S303 are the same as those according to the first embodiment, and thus the description thereof will be omitted.

S904

The feature amount calculation unit 403 calculates the feature amount related to the tumor region extracted in S303, that is, a tumor property feature amount, a tumor-organ feature amount, and an intermediate layer feature amount.

Figure 10:
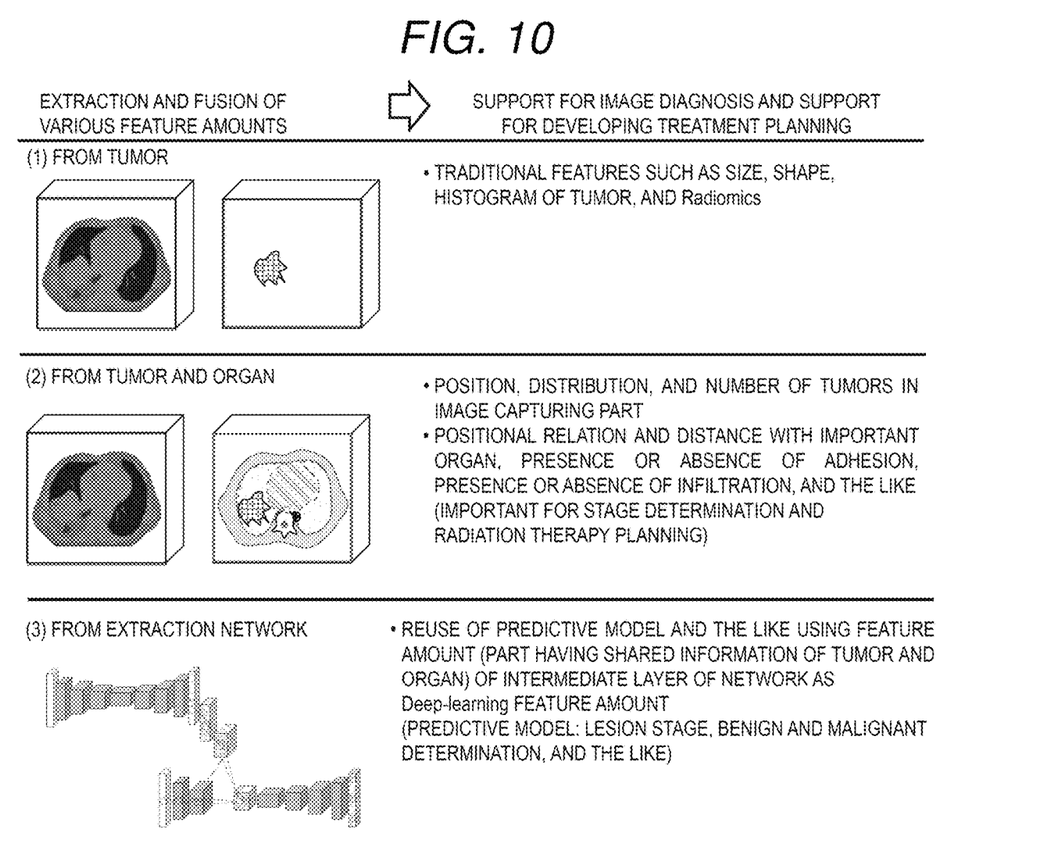
FIG. 10 is a diagram showing an example of a feature amount.

An example of the feature amount calculated by the feature amount calculation unit 403 will be described with reference to FIG. 10. The tumor property feature amount is, for example, a value indicating a size of each tumor region, a value indicating a shape, a value calculated based on a luminance histogram, or Radomics. The value indicating the size of the tumor region includes a volume and a maximum diameter. The value indicating the shape of the tumor region includes an index value indicating circularity or the presence or absence of a cavity. The value calculated based on the luminance histogram includes uniformity of a luminance value and a half-value width of a maximum peak. The tumor property feature amount is used to support the image diagnosis.

The tumor-organ feature amount is, for example, a distance between a tumor region and an organ region, an index value indicating the presence or absence of adhesion, or an index value indicating the presence or absence of infiltration. A position, a distribution, the number, and the like of the tumor in an image capturing part may be included in the tumor-organ feature amount. The tumor-organ feature amount is used to support the image diagnosis and the treatment planning.

The intermediate layer feature amount is a value or the like indicating information shared by the tumor region and the organ region. The intermediate layer feature amount is used for metastasis learning and prediction of a therapeutic effect.

Figure 9:
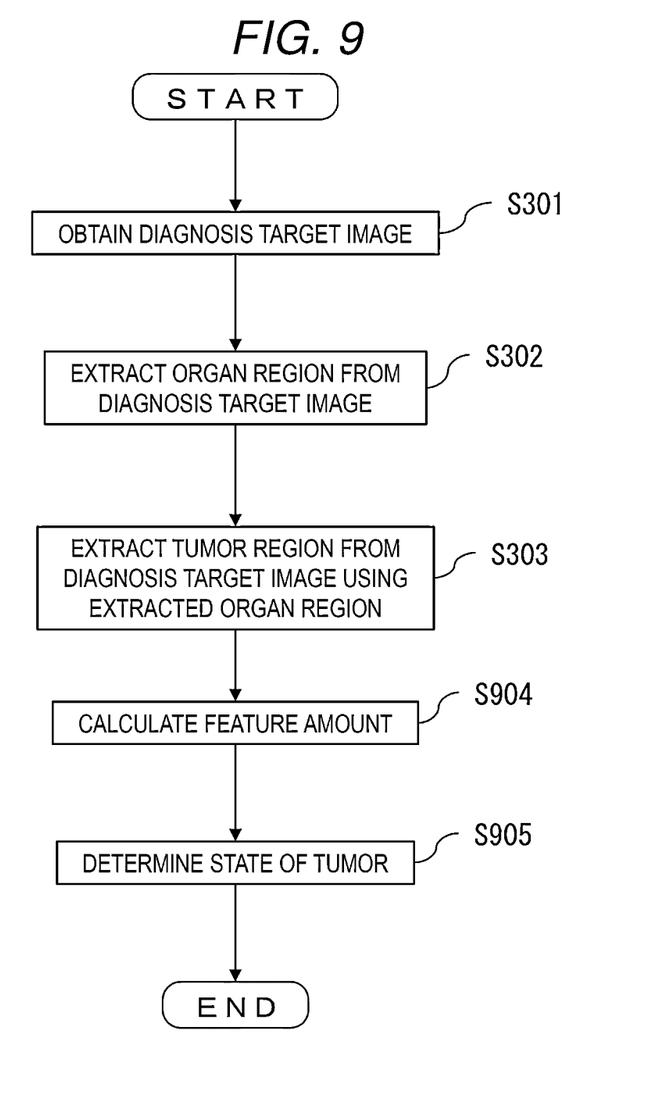
FIG. 9 is a diagram showing an example of a processing flow according to the second embodiment.

The description returns to FIG. 9.

S905

The state determination unit 404 determines the state of the tumor region based on the feature amount calculated in S904. S905 is not essential.

According to the processing flow described above, the tumor region is extracted from the diagnosis target image, the feature amount related to the tumor region is calculated, and the state of the tumor is determined. In the second embodiment, similar to the first embodiment, the tumor region is extracted with high accuracy. The feature amount related to the tumor region calculated by the feature amount calculation unit 403 is used to support the image diagnosis and the treatment planning.

An example of an input and output screen according to the second embodiment will be described with reference to FIG. 11. An input and output screen 500 shown in FIG. 11 includes an axial image display part 511, a sagittal image display part 512, a coronal image display part 513, a three-dimensional image display part 514, a feature amount display part 515, and a determination result display part 516.

The axial image display part 511 displays an axial image of the diagnosis target image. The sagittal image display part 512 displays a sagittal image of the diagnosis target image. The coronal image display part 513 displays a coronal image of the diagnosis target image. A line indicating a contour of the extracted organ region or tumor region may be superimposed and displayed on the axial image, the sagittal image, or the coronal image. The three-dimensional image display part 514 displays a three-dimensional image of the diagnosis target image.

The feature amount display part 515 displays the feature amount calculated by the feature amount calculation unit 403. The feature amount display part 515 shown in FIG. 11 displays that a tumor size is 28 mm, a side edge is a leaflet, there is no air inclusion, the luminance distribution is solid, there is adhesion with the lungs, there is no adhesion with the heart, and the like. The determination result display part 516 displays the state of the tumor region determined by the state determination unit 404. The determination result display unit 516 shown in FIG. 11 displays that a stage is IIIb and the classification is large cells.

The input and output screen 500 includes an image selection button 521, an region extraction button 522, an region selection button 523, an region edit button 524, a feature amount setting button 525, a result output button 526, and a state determination button 527.

The image selection button 521 is used to select a diagnosis target image. The selected diagnosis target image is displayed on the axial image display part 511, the sagittal image display part 512, the coronal image display part 513, and the three-dimensional image display part 514.

The region extraction button 522 is used to extract an organ region or a tumor region from the diagnosis target image. The extracted organ region and tumor region are superimposed and displayed on the axial image display part 511, the sagittal image display part 512, and the coronal image display part 513.

The region selection button 523 is used to select the extracted organ region and tumor region. The region edit button 524 is used to edit the extracted organ region and tumor region. The selection and the editing of the organ region and the tumor region are executed in the axial image display part 511, the sagittal image display part 512, and the coronal image display part 513.

The feature amount setting button 525 is used to set the feature amount related to the tumor region. The set feature amount is calculated by the feature amount calculation unit 403 and displayed on the feature amount display part 515.

The result output button 526 is used to output an extraction result of the organ region and the tumor region and a calculation result of the feature amount from the medical image processing apparatus 1.

The state determination button 527 is used to determine the state of the tumor region. The state of the tumor region is determined by the state determination unit 404 and displayed on the determination result display part 516.

Figure 11:
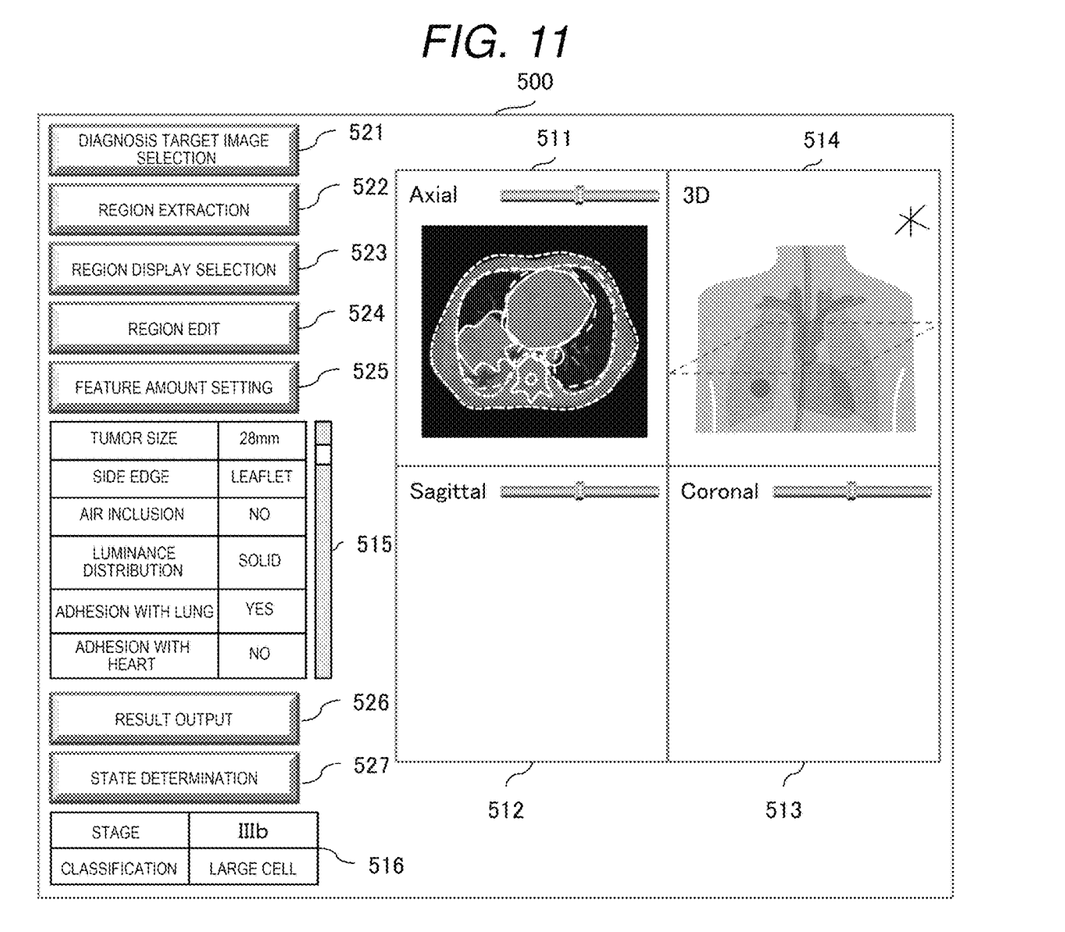
FIG. 11 is a diagram showing an example of an input and output screen according to the second embodiment.

By using the input and output screen 500 shown in FIG. 11, the operator can select a diagnosis target image or check the tumor region extracted from the diagnosis target image together with the feature amount related to the tumor region.

As described above, a plurality of embodiments of the invention have been described. The invention is not limited to the above embodiments, and can be embodied by modifying constituent elements without departing from a spirit of the invention. A plurality of constituent elements disclosed in the above embodiments may be appropriately combined. Further, some constituent elements may be deleted from all the constituent elements shown in the above embodiments.

What is claimed is:

1. A medical image processing apparatus configured to extract a predetermined region from a diagnosis target image, the medical image processing apparatus comprising:
   an organ extraction unit configured to extract an organ region from the diagnosis target image; and
   a tumor extraction unit generated by executing machine learning using a known tumor region included in each medical image group as teacher data and using an organ region extracted from the medical image group and the medical image group as input data,
   wherein the tumor extraction unit is configured to extract a tumor region from the diagnosis target image using the organ region extracted from the diagnosis target image by the organ extraction unit,
   wherein the medical image processing apparatus further comprises a feature amount calculation unit configured to calculate a feature amount related to the tumor region extracted by the tumor extraction unit,
   wherein the feature amount calculated by the feature amount calculation unit includes a tumor-organ feature amount that is a feature amount representing a relation between the organ region extracted from the medical image group, which is extracted by the organ extraction unit, and the tumor region extracted by the tumor extraction unit, and
   wherein the tumor-organ feature amount includes a distance between the organ region and the tumor region, presence or absence of adhesion between the organ region and the tumor region, and presence or absence of infiltration of the tumor region into the organ region.

2. The medical image processing apparatus according to claim 1,
   wherein the organ extraction unit is generated by executing machine learning using a known organ region included in each medical image group as teacher data and using the medical image group as input data, and
   wherein the input data used for generation of the tumor extraction unit includes the organ region extracted from the medical image group by the organ extraction unit.

3. The medical image processing apparatus according to claim 1, wherein
   the feature amount calculated by the feature amount calculation unit includes a tumor property feature amount that is a feature amount related to the tumor region itself extracted by the tumor extraction unit.

4. The medical image processing apparatus according to claim 3,
wherein the tumor property feature amount includes a histogram of a size, a shape, and a pixel value of the tumor region.

5. The medical image processing apparatus according to claim 1, further comprising
a state determination unit configured to determine a state of the tumor region based on the feature amount calculated by the feature amount calculation unit.

* * * * *